(12) United States Patent
Saitoh (10) Patent No.: US 7,477,387 B2
(45) Date of Patent: Jan. 13, 2009

(54) METHOD AND APPARATUS FOR ANALYZING OPTICAL CHARACTERISTICS OF OPTICAL MEDIUM AND METHOD FOR PRODUCTION MONITORING

(75) Inventor: Yukito Saitoh, Minami-ashigara (JP)

(73) Assignee: Fujifilm Corporation, Minato-Ku, Tokyo (JP)

( * ) Notice: Subject to any disclaimer, the term of this patent is extended or adjusted under 35 U.S.C. 154(b) by 342 days.

(21) Appl. No.: 11/366,601

(22) Filed: Mar. 3, 2006

(65) Prior Publication Data

US 2006/0215158 A1    Sep. 28, 2006

(30) Foreign Application Priority Data

Mar. 3, 2005    (JP)    ............... 2005-058434

(51) Int. Cl.
*G01J 4/00* (2006.01)
*G01N 21/00* (2006.01)

(52) U.S. Cl. ..................... 356/364; 356/73.1
(58) Field of Classification Search .......... 356/364–369
See application file for complete search history.

(56) References Cited

U.S. PATENT DOCUMENTS 5,965,874 A * 10/1999  Aso et al. ................... 250/225

6,724,468 B2 * 4/2004  McAlexander et al. ..... 356/73.1
6,888,625 B2 * 5/2005  Anderson ................... 356/73.1

OTHER PUBLICATIONS

Claire Gu et al., "Extended Jones Matrix Method. II", J. Opt. Soc. Am, vol. 10, No. 5, May 1993, pp. 966-973.

* cited by examiner

*Primary Examiner*—Tarifur Chowdhury
*Assistant Examiner*—Tara S Pajoohi
(74) *Attorney, Agent, or Firm*—Buchanan Ingersoll & Rooney PC

(57) ABSTRACT

A novel method for analyzing optical characteristics of an optical medium including illuminating an optical medium, having an input surface and an output surface of light, with at least three input light beams differed from each other in a polarization state, respectively from a direction inclined by a polar angle θ (0°<θ<90°) with regard to the input surface; obtaining polarization states of output light beams coming out from the output surface, corresponded to the input light beams; and determining the Jones matrix M which can satisfy the equation (1) below with polarization vectors of the input light beams and polarization vectors of the output light beams:

$$\begin{pmatrix} Es' \\ Ep' \end{pmatrix} = Q' \times M \times Q \times \begin{pmatrix} Es \\ Ep \end{pmatrix} \quad (1)$$

9 Claims, 5 Drawing Sheets

METHOD AND APPARATUS FOR ANALYZING OPTICAL CHARACTERISTICS OF OPTICAL MEDIUM AND METHOD FOR PRODUCTION MONITORING

CROSS-REFERENCE TO RELATED APPLICATIONS

This application claims benefit of priority under 35 USC 119 to Japanese Patent Application No. 2005-058434 filed Mar. 3, 2005.

TECHNICAL FIELD OF THE INVENTION

The present invention relates to a method for analyzing optical characteristics of optical mediums, and in particular to a method for analyzing optical characteristics of optical films useful for development and design of liquid crystal display devices. The present invention also relates to an apparatus for analyzing an optical medium employing the above-described analytical method, and a method for production monitoring.

RELATED ART

A liquid crystal display device usually comprises a liquid crystal cell and polarizing plates. The polarizing plate usually has protective films and a polarizing film, and is obtained typically by dying the polarizing film composed of a polyvinyl alcohol film with iodine, stretching, and being stacked on both surfaces thereof with the protective films. A transmissive liquid crystal display device usually comprises polarizing plates on both sides of the liquid crystal cell, and occasionally comprises one or more optical compensation films. A reflective liquid crystal display device usually comprises a reflector plate, the liquid crystal cell, one or more optical compensation films, and a polarizing plate in this order. The liquid crystal cell comprises liquid-crystalline molecules, two substrates encapsulating the liquid-crystalline molecules, and electrode layers applying voltage to the liquid-crystalline molecules. The liquid crystal cell switches ON and OFF displays depending on variation in orientation state of the liquid-crystalline molecules, and is applicable both to transmission type and reflective type, of which display modes ever proposed include TN (twisted nematic), IPS (in-plane switching), OCB (optically compensatory bend) and VA (vertically aligned), and ECB (electrically controlled birefringence).

Various LCDs, which are required to exhibit high display qualities, are generally improved in viewing angle by optical compensation films. In particular, 90° twisted nematic liquid crystal display devices (referred to as TN-mode, hereinafter), employing nematic liquid crystal molecules having a positive dielectric anisotropy and driven by thin-film transistors, are usually improved by optical compensation films prepared by using discotic compounds, and those based on the OCB mode (or bend mode), characterized in their rapid response are optically compensated by the methods described in Japanese Laid-Open Patent Publication "Tokkaihei" Nos. 9-211444, 11-316378, and so forth.

The conventional optical films employed for this purpose have occasionally been defined by a uniaxial birefringent medium, a biaxial birefringent medium, or a stack of these media, and, so far, optical characteristics of a liquid crystal display employing optical film(s) have been evaluated by calculating a propagation matrix at oblique angle with a uniaxial or biaxial model or N-stacked layer model. Conventional methods for studying polarization states of light employing these models are described in "Kessho Kogaku (Crystal Optics)", edited by Optics Conversazione of the Japan Society of Applied Physics, published by Morikita Shuppan Co., Ltd. (1975); A. Lien, Appl. Phys. Lett. Vol. 57, (1990) 2667; P. Yeh, J. Opt. Soc. Am., Vol. 72, (1982) 507; P. Yeh, J. Opt. Soc. Am., Vol. 10, (1993) 966; and D. W. Berreman, J. Opt. Soc. Am., Vol. 62, (1972) 502.

It is, however, difficult for these methods to exactly express the optical characteristics of the actual optical films. Because of complexity of internal structures of the actual optical films (see Y. Takahashi, H. Watanabe, T. Kato: Proc. Jpn. Liq. Cryst. Conf. (2003) p.194, for example), these models, such as a simple uniaxial model or a biaxial model, are insufficient to describe the actual film properties. It is also difficult to express an exact internal micro-structure of an actual optical film with a multi-layered birefringent media model having an optical axis.

SUMMARY OF THE INVENTION

It is therefore an object of the present invention to provide a method for measuring optical characteristics at, under oblique incidence of light, of an optical medium by obtaining the Jones matrix at an oblique angle of an optical medium capable of polarization conversion, using vectors of light obliquely incident on the optical medium and measured vectors of the output light. It is another object of the present invention to provide a method and an apparatus capable of exactly analyzing the optical characteristics of an optical medium having polarization conversion properties, without using any conventional uniaxial, biaxial and multi-layered models. It is still another object of the present invention to provide a method for stably producing optical mediums exhibiting uniform optical properties.

In one aspect, the present invention provides a method for analyzing optical characteristics of an optical medium comprising:

illuminating an optical medium, having an input surface and an output surface of light, with at least three input light beams differed from each other in a polarization state, respectively from a direction inclined by a polar angle θ (0°<θ<90°) with regard to the input surface;

obtaining polarization states of output light beams coming out from the output surface, corresponded to the input light beams; and determining the Jones matrix M which can satisfy the equazion (1) below with polarization vectors of the input light beams and polarization vectors of the output light beams:

$$\begin{pmatrix} Es' \\ Ep' \end{pmatrix} = Q' \times M \times Q \times \begin{pmatrix} Es \\ Ep \end{pmatrix} \quad (1)$$

where, Es and Ep are polarization vectors of s-polarization and p-polarization of an input light beam, respectively; Es' and Ep' are polarization vectors of s-polarization and p-polarization of a correspondent output light beam, respectively; Q is a dynamics matrix expressing change in a polarization state of an input light beam going into the optical medium from the air; and Q' is a dynamics matrix expressing change in a polarization state of an output light beam going out the optical medium into the air.

As embodiments of the present invention, there are provided the method using matrices expressed by formulae (q1) and (q2) below for Q and Q', respectively, given that the birefringence of the optical medium is approximately 0.1 or smaller:

$$\begin{pmatrix} \frac{2n\cos\theta}{n\cos\theta + n_o\cos\theta_o} & 0 \\ 0 & \frac{2n\cos\theta}{n\cos\theta_o + n_o\cos\theta} \end{pmatrix} \quad (q1)$$

$$\begin{pmatrix} \frac{2n_o\cos\theta_o}{n_o\cos\theta_o + n\cos\theta} & 0 \\ 0 & \frac{2n_o\cos\theta_o}{n_o\cos\theta + n\cos\theta_o} \end{pmatrix} \quad (q2)$$

where, n is the refractive index of air, $n_o$ is a mean refractive index of the optical medium to be measured, $\theta$ is an incidence angle, and $\theta_0$ is a refraction angle of light in the optical medium; the method further comprising calculating the Stokes parameters as Es, Ep, Es' and Ep' so as to express polarization characteristics of Es, Ep, Es' and Ep'; the method further comprising illuminating the optical medium with at least three input light beams, differed from each other in a polarization state, at least at two azimuthal angles $\phi$ (0°<$\phi$<360°), to thereby respectively obtain the Jones matrices which satisfy the equation (1); and obtaining an azimuthal angle dependence of at least one parameter which determines the Jones matrices; and the method further comprising illuminating the optical medium with at least three light beams differed from each other in a polarization state, from at least two directions differing in polar angle $\theta$ (0°<$\theta$<90°), to thereby respectively obtain the Jones matrices which satisfy the equation (1); and obtaining a polar angle dependence of at least one parameter which determines the Jones matrices.

In another aspect, the present invention provides an apparatus for analyzing an optical medium, comprising:

a light source;

an input unit allowing at least three input light beams from the light source, differed from each other in a polarization state, to enter a surface of an optical medium from a direction inclined by a polar angle $\theta$ (0°<$\theta$<90°) with regard to the surface;

a detection unit detecting polarization states of output light beams from the optical medium, corresponded to the input light beams; and a calculation unit determining the Jones matrix M which can satisfy the equation (1) below with polarization vectors of the input light beams and polarization vectors of the correspondent output light beams:

$$\begin{pmatrix} Es' \\ Ep' \end{pmatrix} = Q' \times M \times Q \times \begin{pmatrix} Es \\ Ep \end{pmatrix} \quad (1)$$

where, Es and Ep are polarization vectors of s-polarization and p-polarization of an input light, respectively; Es' and Ep' are polarization vectors of s-polarization and p-polarization of a correspondent output light beam, respectively; Q is a dynamics matrix expressing changes in a polarization state of a input light beam going into an optical medium from the air; and Q' is a dynamics matrix expressing changes in a polarization state of an output light beam going from the optical medium into the air.

As embodiments of the present invention, there are provided the apparatus wherein the input unit is capable of allowing at least three input light beams, differed from each other in a polarization state, to enter a surface of an optical medium from at least two directions differing in polar angle $\theta$ (0°<$\theta$<90°) and/or azimuthal angle $\phi$ (0°<$\phi$<360°); and the apparatus further comprising an output unit outputting a graphical expression of at least one parameter of the Jones matrix determined by the calculation unit plotted with respect to polar angle $\theta$ and/or azimuthal angle $\phi$.

In another aspect, the present invention provides a method for production monitoring of an optical medium comprising:

illuminating an optical medium, having an input surface and an output surface of light, with at least three input light beams differed from each other in a polarization state, respectively from a direction inclined by a polar angle $\theta$ (0°<$\theta$<90°) with regard to the input surface;

obtaining polarization states of output light beams coming out from the output surface, corresponded to the input light beams;

determining the Jones matrix M which can satisfy the equation (1) below with polarization vectors of the input light beams and polarization vectors of the output light beams; and monitoring a shift from an ideal value of at least one parameter which determines the Jones matrix M:

$$\begin{pmatrix} Es' \\ Ep' \end{pmatrix} = Q' \times M \times Q \times \begin{pmatrix} Es \\ Ep \end{pmatrix} \quad (1)$$

where, Es and Ep are polarization vectors of s-polarization and p-polarization of an input light beam, respectively; Es' and Ep' are polarization vectors of s-polarization and p-polarization of an output light beam, respectively; Q is a dynamics matrix expressing change in a polarization state of an input light beam going into an optical medium from the air; and Q' is a dynamics matrix expressing change in a polarization state of an output light beam going from the optical medium into the air.

According to the present invention, optical characteristics of an optical medium is analyzed by determining the Jones matrix which expresses transformations in polarization state of an obliquely incident light, without using any conventional uniaxial, biaxial or multi-layered model. As a result, the present invention can produce excellent effects of making it possible to more exactly express the optical characteristics of the optical medium, and to more precisely design displays based on characteristics of the actual film. The present invention can also provide a method for production monitoring contributive to improvements in production stability of optical mediums.

Reference numerals used in the drawings express the followings:

10 sample (optical medium);

12 light source, 14 detector; and
16 calculator.

DETAILED DESCRIPTION OF THE INVENTION

Hereafter, the present invention will be explained in detail, referring to formulae and the attached drawings.

The present invention relates to a method for analyzing optical characteristics of an optical medium, which has optical characteristics of transforming polarization state, such as an optical compensation film used for liquid crystal displays. The Jones matrix M of an optical medium which has optical characteristics of transforming polarization state, such as an optical compensation film used for liquid crystal displays is a unitary matrix, and can be described as below when the optical medium is a non-absorbing medium:

$$M = \begin{pmatrix} a+ib & c+id \\ -c+id & a-ib \end{pmatrix} \quad (2)$$

where a, b, c and d are real numbers, which are required to satisfy the relation given by the equation (3) below:

$$a^2+b^2+c^2+d^2=1 \quad (3).$$

Therefore, the number of independent parameters of a, b, c and d is three.

Unlike for the case of normal incidence of light, for the case of oblique incidence of light, it is necessary to consider both of s-polarization and p-polarization vectors. It is also necessary to consider the Fresnel transmission coefficients at the air-film interface. Based on these considerations, an idea of the extended Jones matrix is introduced (see P. Yeh, J. Opt. Soc. Am., Vol. 72, (1982) 507; P. Yeh, J. Opt. Soc. Am., Vol. 10, (1993) 966). More specifically, an assumption can be made that there is a zero-trickness fictitious isotropic layer between the optical media. Another assumption is that the birefringence, or anisotropy, of the optical medium to be measured is as small as being negligible (P. Yeh, J. Opt. Soc. Am., Vol. 72, (see 1982) 507; and P. Yeh, J. Opt. Soc. Am., Vol. 10, (1993) 966). In this case, a propagation matrix which correlates the polarization characteristics of the incoming light with the polarization characteristics of the outgoing light is simply given by the equation (1) below:

$$\begin{pmatrix} Es' \\ Ep' \end{pmatrix} = Q' \times M \times Q \times \begin{pmatrix} Es \\ Ep \end{pmatrix} \quad (1)$$

where, Es and Ep are polarization vectors of s-polarization and p-polarization of the incoming light, respectively; Es' and Ep' are polarization vectors of s-polarization and p-polarization of the outgoing light, respectively; Q is a dynamics matrix expressing changes in the polarization state of the light coming into the optical medium from the air; and Q' is a dynamics matrix expressing changes in the polarization state of light going out from the optical medium into the air.

According to the present invention, an optical medium is illuminated with at least three input light beams differed from each other in the polarization state, respectively from a direction inclined by a polar angle θ (0°<θ<90°), so as to obtain polarization states of the output light beams corresponded to the respective input light beams, and the Jones matrix M which can satisfy the above-described equation (1) with polarization vectors (Es, Ep) of the input light beams and polarization vectors (Es', Ep') of the output light beams corresponded to the respective input light beams. According to the present invention, without using uniaxial, biaxial and multi-layered models which have been used in the conventional analysis, the Jones matrix M in which actual optical characteristics are more exactly reflected can be determined.

It is to be noted herein that "polar angle" denotes inclination in the z-axis direction assuming the input surface of the optical medium as an x-y plane, wherein polar angle=0° means the direction in parallel with the input surface, and polar angle=90° means the direction coincides with the normal line on the input surface.

Given that the birefringence of the optical medium is as small as approximately 0.1 or below, Q can be approximated by the matrix written as formula (q1) below, and Q' can be approximated by the matrix written as formula (q2) below, respectively using the Fresnel transmission coefficients:

$$\begin{pmatrix} \frac{2n\cos\theta}{n\cos\theta + n_o\cos\theta_o} & 0 \\ 0 & \frac{2n\cos\theta}{n\cos\theta_o + n_o\cos\theta} \end{pmatrix} \quad (q1)$$

$$\begin{pmatrix} \frac{2n_o\cos\theta_o}{n_o\cos\theta_o + n\cos\theta} & 0 \\ 0 & \frac{2n_o\cos\theta_o}{n_o\cos\theta + n\cos\theta_o} \end{pmatrix} \quad (q2)$$

where, n is the refractive index of air, $n_o$ is a mean refractive index of an optical medium to be measured, θ is an angle of light incidence, and $\theta_0$ is a refraction angle of light in the optical medium.

The equation (1) in the above is therefore given as the equation (1') below, in which ts', tp', ts and tp are respectively expressed by the equations (4) to (7):

$$\begin{pmatrix} E'_s \\ E'_p \end{pmatrix} = \begin{pmatrix} t'_s & 0 \\ 0 & t'_p \end{pmatrix} M \begin{pmatrix} t_s & 0 \\ 0 & t_p \end{pmatrix} \begin{pmatrix} E_s \\ E_p \end{pmatrix}, \quad (1')$$

$$t'_s = \frac{2n_o\cos\theta_o}{n_o\cos\theta_o + n\cos\theta} \quad (4)$$

$$t'_p = \frac{2n_o\cos\theta_o}{n_o\cos\theta + n\cos\theta_o} \quad (5)$$

$$t_s = \frac{2n\cos\theta}{n\cos\theta + n_o\cos\theta_o} \quad (6)$$

$$t_p = \frac{2n\cos\theta}{n\cos\theta_o + n_o\cos\theta} \quad (7)$$

With the equation (1) in the above (equation (1') for the case where the birefringence of the optical medium is as small as approximately 0.1 or below), the relation between the polarization states of the incoming light and on the outgoing light can be expressed. The present invention provides a novel method for measuring optical characteristics of the optical medium at oblique light incidence, and, in particular, a novel method comprising determining the Jones matrix of an optical medium at oblique light incidence by employing the relation.

As described later, the polarization vectors of the input and output light beams can be obtained by using an ellipsometer as the Stokes parameters ($S_1$, $S_2$, $S_3$) which are functions of incidence angle. It is also allowable in the analytical method of the present invention to respectively calculate the Stokes parameters of the input and output light beams, to thereby describe the polarization characteristics of Es, Ep, Es' and Ep' for the analysis.

It is also made possible to obtain azimuthal angle dependence of at least one parameters from a, b, c and d which determine the Jones matrix M, by illuminating the optical medium with at least three input light beams differed from each other in the polarization state, from at least two directions differing in the azimuthal angle φ (0°<φ<360°), to thereby respectively obtain the Jones matrices which satisfy the equation (1). It is still also made possible to obtain polar-angle dependence of at least one parameters from a, b, c and d which determine the Jones matrix M, by illuminating the optical medium with at least three input light beams differed from each other in the polarization state, from at least two directions differing in the polar angle θ (0°<θ<90°), to thereby respectively obtain the Jones matrices which satisfy the equation (1). It is therefore made possible to know the azimuthal angle dependence or the polar angle dependence of the above-described parameters a, b, c and d over the entire ranges of azimuthal angle (0° to 360°) and polar angle (0° to 90°), and consequently to obtain a complete characteristic map of the optical medium.

It is to be noted herein that azimuthal angle means inclination from one of axes that run at right angles to one another in the input surface, and is typically means an angle counter-clock wisely away from the x-axis, when the optical medium is viewed towards the input surface, assuming the horizontal direction thereof as the x-axis and the right-hand side thereof as plus (+).

A flow of analysis of the present invention will now be explained referring to FIG. 1 and FIG. 2.

Figure 1:
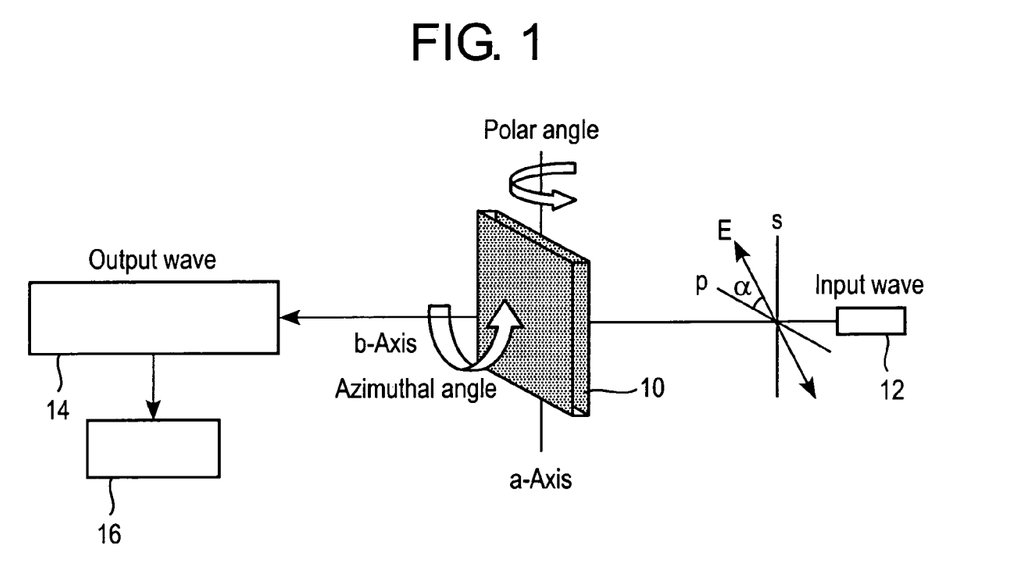
FIG. 1 is a simplified schematic drawing of an exemplary configuration of a device employing the analytical method of the present invention.

FIG. 1 is a schematic drawing showing an exemplary analyzer employing the analytical method of the present invention.

The analyzer shown in FIG. 1 comprises a light source 12, and a support member (not shown) rotationally supporting a sample 10 such as an optical film, and allows light from the light source 12 to illuminate the sample 10 at a predetermined polar angle θ (0°<θ<90°) by rotating the sample 10 around the a-axis. The support member may also have a mechanism which allows light from the light source 12 to illuminate the sample 10 at a predetermined azimuthal angle φ (0°<φ<360°) by rotating the sample 10 around the b-axis. The polarization angle α of a light beam from the light source 12 incident on the sample 10 may be adjustable to a predetermined angle typically with the aid of a mechanism owned by the light source 12 per se, or polarizing plate, filter or the like disposed between the light source 12 and the sample 10

The input light beam incident on the sample 10 with a polarization angle of α goes out form the sample 10 after being transformed in the polarization state thereof during transmission there through, and is detected by a detector 14. If the detector 14 is an ellipsometer, the Stokes parameters $S_1$, $S_2$, $S_3$, which are functions of polarization angle α of the input light beam, are typically measured. The Stokes parameters of the output light beam, obtained under incidence of a plurality of (at least three) input light beams, differed from each other in the polarization state (polarization angle), are then input to a calculator 16, and the calculator 16 fits the input Stokes parameters using the equation (1), to thereby calculate the Jones matrix (a, b, c, d).

Figure 2:
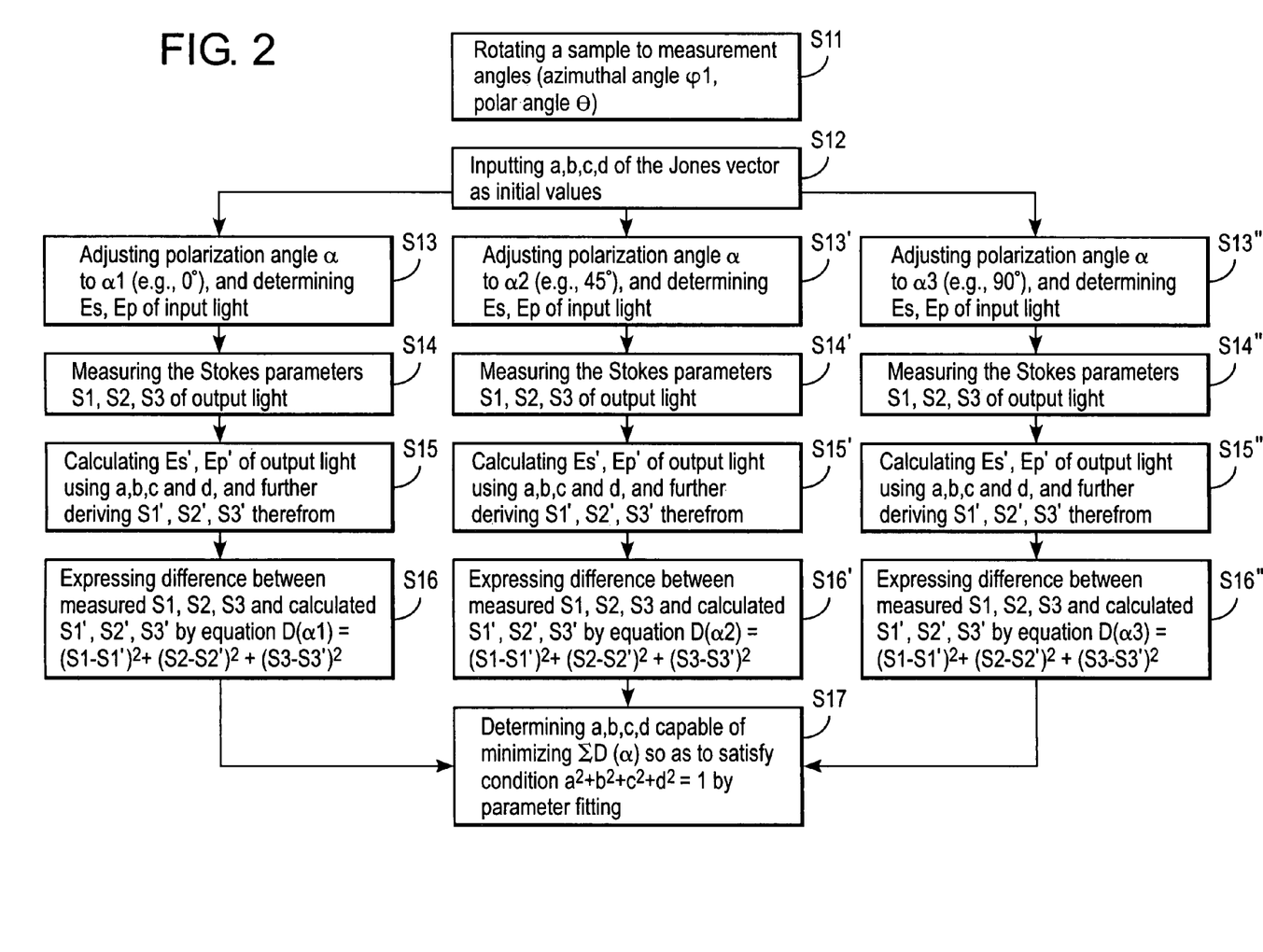
FIG. 2 is an exemplary flow chart of the analytical method of the present invention.
Figure 3A:
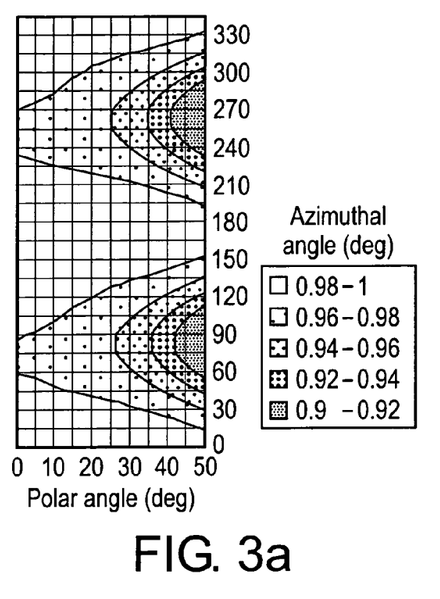
FIGS. 3A to 3D are drawings showing results of measurement in Example 1.
Figure 3B:
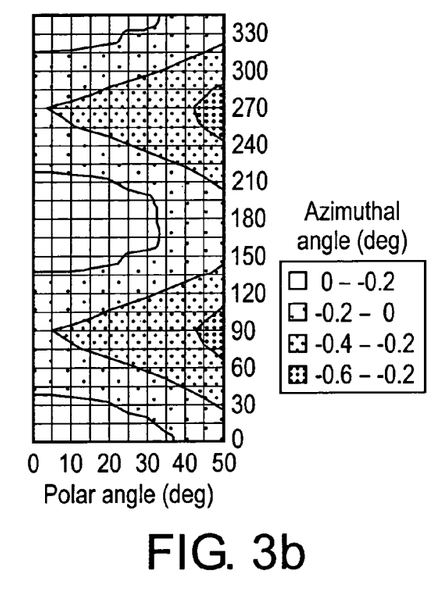
Figure 3C:
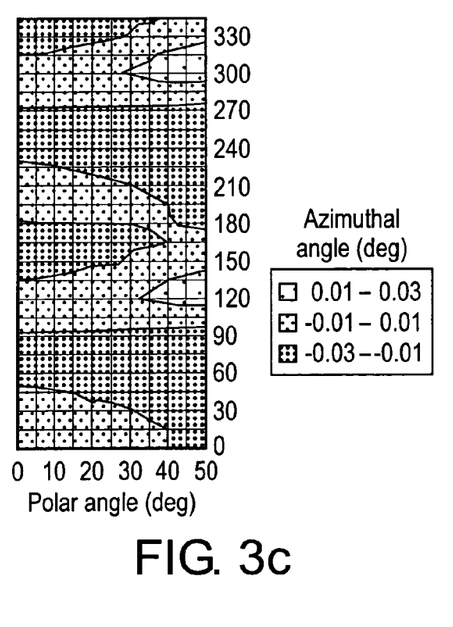
Figure 3D:
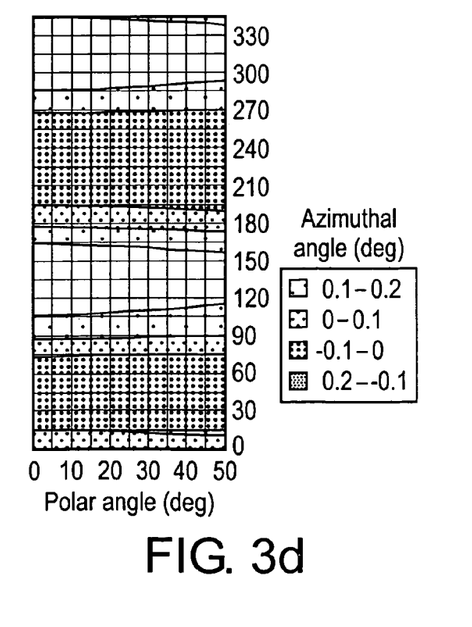
Figure 4A:
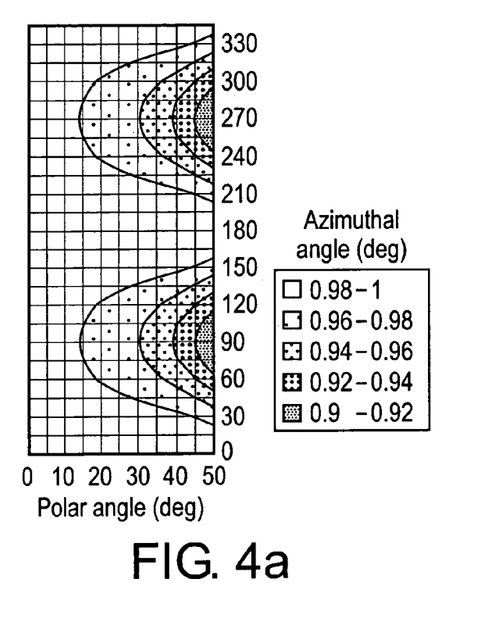
FIGS. 4A to 4D are drawings showing results obtained by using a conventional model, aimed at explaining effects of the results of measurement in Example 1.
Figure 4B:
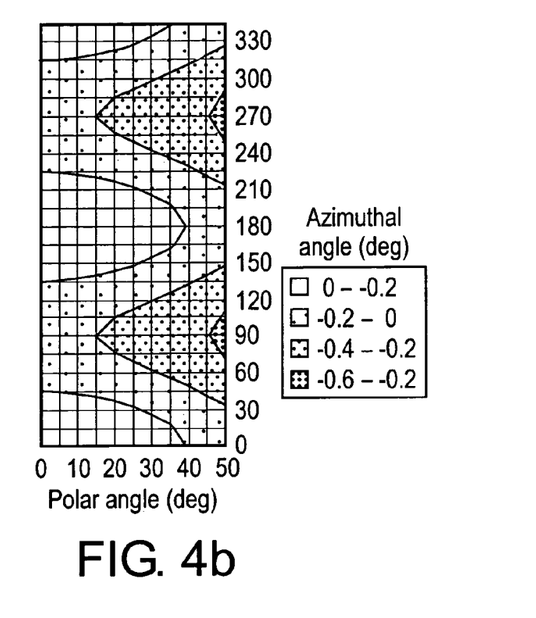
Figure 4C:
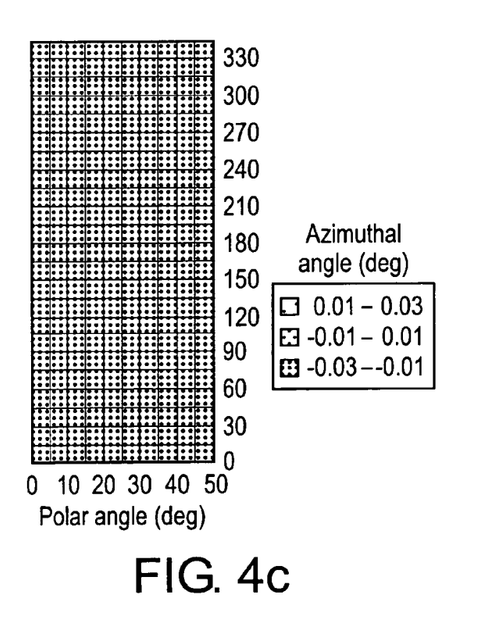
Figure 4D:
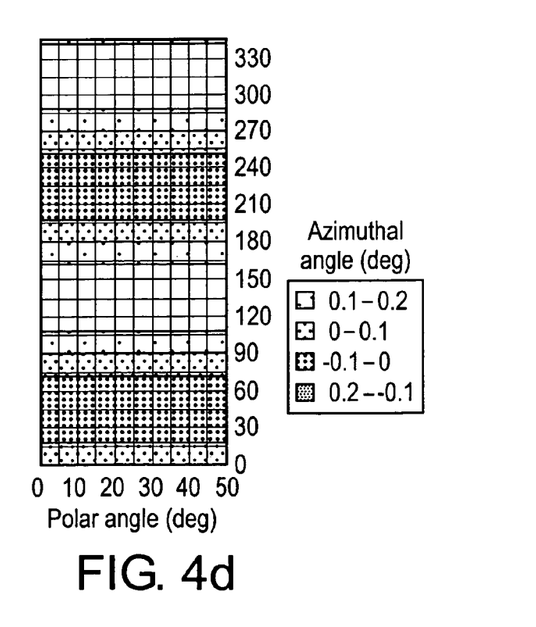

The flow of the analytical method of the present invention will more specifically be described referring to FIG. 2.

First, the support member is rotated by the polar angle θ and by the azimuthal angle φ with regard to a light beam being emitted from the light source 12 and going into the sample 10, and the sample 10 is fixed (step 11: S11). Assumptive values of a, b, c and d of the Jones matrix M are then input as initial values to the calculator 16 (step 12: S12). Next, Es and Ep are calculated for a light beam having polarization angle α1 (0°, for example) going into the sample 10, and are similarly input to the calculator 16 (step 13: S13). Assuming now that the polarization angle of an input light beam is α1, Es and Ep expressing polarization state of the output light beam can be given as Es=sin α1 and Ep=cos α1, which are again input to the calculator 16. A polarized light from the light source 12, having a polarization angle of α1, is then actually allowed to illuminate the sample 10 at polar angle θ and azimuthal angle φ, the Stokes parameters $S_1$, $S_2$ and $S_3$ of the output light are measured by a detector 14 such as an ellipsometer (step 14: S14) and then input to the calculator 16. Besides such Stokes parameters $S_1$, $S_2$ and $S_3$ derived from the actual measurement, the Stokes parameters $S_1'$, $S_2'$ and $S_3'$ are calculated from the initial values for a, b, c and d input in step 12 (step 15: S15). Difference between the Stokes parameters $S_1$, $S_2$ and $S_3$ derived from the measured values and the Stokes parameters $S_1'$, $S_2'$ and $S_3'$ obtained by calculation is expressed by the equation (8) below:

$$D(\alpha 1)=(S_1-S_1')^2+(S_2-S_2')^2+(S_3-S_3')^2 \quad (8)$$

Next, the same processes S13' to S16' are carried out also for an input light beam having a polarization angle of α2 (≠α1, 45° for example), to thereby obtain D(α2) as expressed by the equation (8). Furthermore, the same processes S13" to S16" are carried out also for an input light beam having a polarization angle of α3 (≠α1≠α2, 90° for example), to thereby obtain D (α3) as expressed by the equation (8). At east three polarized light beams differed from each other in the polarization angle α are allowed to illuminate the sample 10 to thereby obtain D(α), and the parameters a, b, c and d capable of minimizing ΣD(α) are determined by parameter fitting, so as to satisfy the condition $a^2+b^2+c^2+d^2=1$ expressed by the equation (3) (step 17: S17). More specifically, S1', S2', S3' and D(α) are re-calculated respectively for at least three different α's, ΣD(α) is re-calculated, and the parameters a, b, c and d capable of minimizing ΣD(α) are determined by parameter fitting under the condition of $a^2+b^2+c^2+d^2=1$.

In such a way, the Jones matrix M necessary for calculating the polarization state of light obliquely incident on the sample 10 at a polar angle of θ, can be obtained without using the conventional model.

In addition, it is also made possible to determine azimuthal angle dependence of the parameters a, b, c and d which determine the Jones matrix M, by repeating the same processes while varying the azimuthal angle φ over the range from 0° to 360°. It is still also possible to determine polar angle dependence of the parameters a, b, c and d which determine the Jones matrix M, by repeating the same processes while varying the polar angle θ over the range from 0 to 90°. For example, a complete characteristic map of the sample 10 can be obtained by plotting the parameters a, b, c and d of the Jones matrix M determined by the calculator 16 with respect to the azimuthal angle φ and/or polar angle φ, and by outputting the results as a graph (for example, such as a graph shown in FIG. 3 obtained in Example 1 described later).

The input light beam, described as being a linear polarized light in the above example, is not always necessarily a linear polarized light, and allows elliptically polarized light and circularly polarized light. Es and Ep in these cases can be expressed by so-called Jones vector description. For example, right-circularly polarized light gives Es=$1/\sqrt{2}$ and Ep=$i/\sqrt{2}$.

The Jones vectors are detailed in "Kessho Kogaku (Crystal Optics)", edited by Optics Conversazione of the Japan Society of Applied Physics, published by Morikita Shuppan Co., Ltd. (1975).

As shown in FIG. 2, it is possible to determine the parameters a, b, c and d, by using at least three independent input light beams differed from each other in the polarization state. It is, however, more desirable to measure the polarization state a possibly maximum number of times, and to carry out the parameter fitting of the parameters a, b, c and d, in view of preventing degradation in accuracy of calculation of the parameters, depending on the angle or ellipticity of the input light beam.

The device making use of the analytical method of the present invention is not limited to that having the configuration shown in FIG. 1, and allows inclusion of other components. For example, as described in the above, it is also allowable to dispose, between the sample 10 and the light source 12, a polarizer film adjusting the polarization angle of the input light beam, and still also allowable to dispose a filter between such polarizer film and the sample 10. It is also allowable to dispose a reflecting plate there between if the measurement is made in a reflection mode.

By using the Jones matrix obtained by measurement of the present invention, it is also made possible to simulate the Jones matrix as if it were a single component. In other words, the Jones matrix, as measured, can be optically simulated unlike the conventional models which involve assumption of a uniaxial or biaxial birefringent medium, or involve assumption of a stack of birefringent media each having an optical axis and birefringence. It is therefore made possible to carry out optical simulation in a manner more closely adopted to the real configuration.

More specifically, by calculating a product of the Jones matrix at any oblique incidence angle, obtained according to the method of the present invention, multiplied by the Jones matrix of other optical component obtained according to the method of the present invention or according to any other method, it is made possible to calculate a light propagation matrix of an optical element such as liquid crystal display. Methods of calculating the propagation matrix at oblique incidence angle adoptable herein are such as those described in P. Yeh, J. Opt. Soc. Am., Vol. 72, (1932) 507; and P. Yeh, J. Opt. Soc. Am., Vol. 10, (1993) 966. Once the propagation matrix is calculated, it is made possible to predict optical characteristics of the optical element, including transmittance, color tone and contrast.

It is also allowable to incorporate the method of measurement and the method of calculation of the present invention into a calculation device of measuring instrument, liquid crystal simulator and the like. This makes it possible to efficiently carry out the methods of the present invention, and can provide a powerful device useful for analysis of optical media such as optical film, or optical design of liquid crystal display.

It is still also allowable to incorporate the above-described device into a production line of optical media such as optical film and liquid crystal cell. More specifically, it is made possible to provide a method for production monitoring of an optical medium which comprises illuminating an optical medium, having an input surface and an output surface of light, with at least three input light beams differed from each other in the polarization state, respectively from a direction inclined by a polar angle θ (0°<θ<90°) with regard to the input surface; obtaining polarization states of output light beams coming out from the output surface, corresponded to the respective input light beams; determining the Jones matrix M which can satisfy the equation (1) in the above with polarization vectors of the input light beams and polarization vectors of the output light beams corresponded to the respective the input light beams: and monitoring a shift from an ideal value of at least one parameter which determines the Jones matrix M. The method of production monitoring makes it possible to immediately feedback results of the monitoring to the relevant process step in the production line, and thereby contributes characteristic monitoring of the products, and failure analysis.

Targets of the analytical method of the present invention are not specifically limited, so far as they are optical media having a function of transforming polarization. For example, the method is applicable to analysis of optical characteristics of various optical media, such as optical compensation film, protective film for polarizer plate, retardation film, liquid crystal cell and polarization control unit, used for liquid crystal display device, liquid crystal polarization control device and other general polarization control devices.

EXAMPLES

The paragraphs below will further detail the present invention referring to Examples. It is to be understood that Examples described below are specific examples of the present invention and the present invention is not limited to the specific examples described below.

Example 1

The Jones matrix of a polymer film was measured using an analyzer configured as shown in FIG. 1. A stretched polymer film (reference numeral 10 in the drawing) was used in the measurement, and the wavelength of the input light was 589 nm. A transmission ellipsometer (reference numeral 14 in the drawing) was used for measurement of the polarization state of the output light. The polymer film was measured by Abbe's method for mean refractive index, and the value was found to be 1.50. Polarization directions α of the input light was varied among 0°, 45°, 90° and 135°, and polarization states, or Stokes parameters ($S_1$, $S_2$, $S_3$), were measured. Thus measured Stokes parameters were then fitted to three parameters using the equation (1) (more specifically, equation (1')) and thereby a, b, c and d were determined. Such measurement was repeated while varying the polar angle θ and the azimuthal angle φ, to thereby determine the unidirectional Jones matrix. The repetitive calculation method based on a quasi-Newton method was used for the parameter fitting.

<Results of Obtained Parameters of the Jones Matrix>

FIG. 3 shows calculated results of the parameters a, b, c and d of the Jones matrix. It is understandable that a complete characteristic map of the film can be obtained for all polar angles θ and azimuthal angles φ, without using the conventional models. As a comparative example, FIG. 9 shows values of a, b, c and d theoretically calculated using a conventional model of biaxial birefringent medium. The values adopted herein were nx=1.5, ny=1.4997, nz=1.4982, and thickness=100 mm. FIG. 3 and FIG. 4 may be looked similar but differ in the profile. In particular, FIG. 4 based on the model of biaxial birefringent medium shows a value of "c" constantly remained zero, which indicates that the eigenvector of the Jones matrix is ascribable to linear polarization irrespective of angle. In contrast to this, the value of "c" is not zero in FIG. 3, showing variation in the value depending on the angle, which indicates that the eigenvector of the Jones matrix is not always ascribable to linear polarization irrespective of angle, and so that the medium cannot be expressed by the biaxial birefringent model. Difference between FIG. 3 and FIG. 4 means difficulty in expressing the real optical medium with the conventional model. It is therefore understandable that the method of the present invention makes it possible to exactly express the real optical medium.

Example 2

Using the Jones matrix obtained in Example 1, characteristics of an optical element, which is a liquid crystal display in this Example, were calculated. A liquid crystal layer employed herein was assumed as being in the vertically-aligned black state, or in other words being under no applied voltage, and the optical compensation in the black state was calculated. The liquid crystal layer was assumed as having a Δn·d of 300 nm, placed between the crossed polarizer plates, and the measured optical media were placed one by one between the upper/lower polarizer plates and the liquid crystal layer. Each optical medium was arranged so that the zero-degree direction of the measured polar angle is aligned in parallel with the transmission axis of each polarizer plate. Transmittance was then calculated while varying the polar angle in the direction 45° away from the transmission axis of the polarizer plate (so-called, off-axis state). The extended Jones matrix method shown in Y. Takahashi, H. Watanabe, T. Kato: Proc. Jpn. Liq. Cryst. Conf. (2003) p.194, was adopted to the calculation of transmittance, and a product of the Jones matrix obtained in Example 1 multiplied by the Jones matrices of the polarizer plates and of the liquid crystal layer separately obtained by the extended Jones matrix method was obtained by calculation. For comparative study, a liquid crystal cell was actually fabricated based on a configuration completely same as that in the calculation, and the transmittance was measured.

<Results of Measurement of Transmittance of the Display Device>

Figure 5:
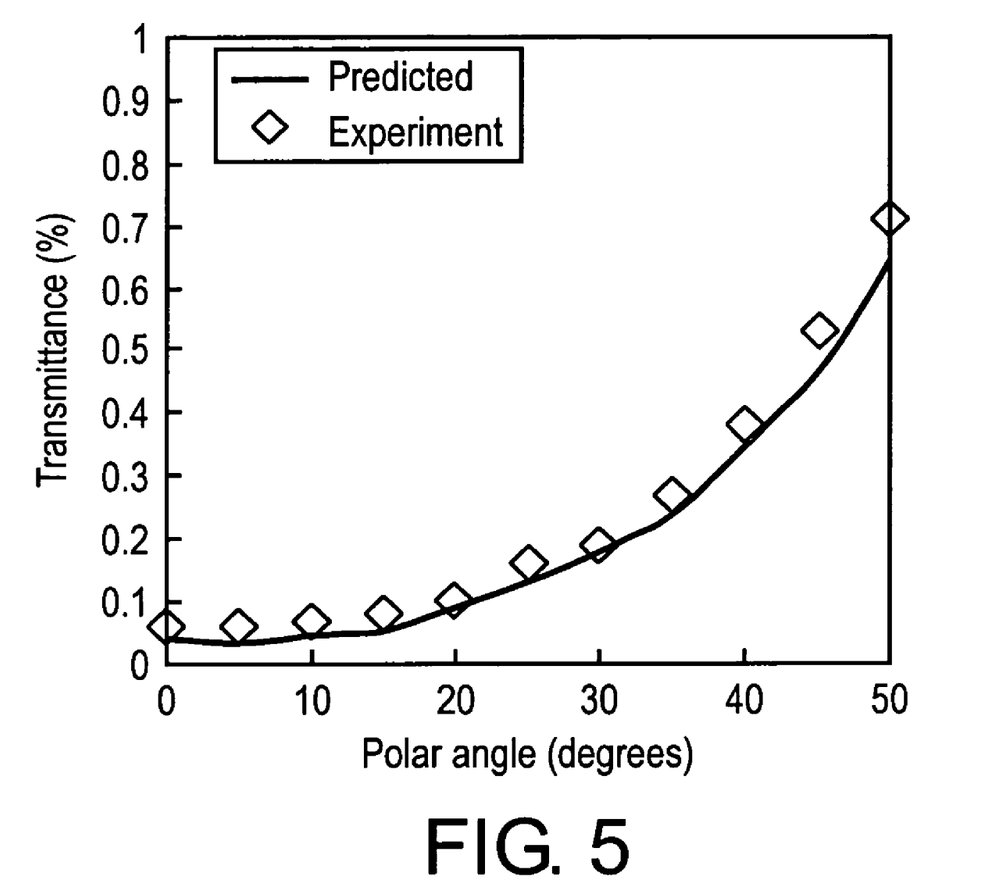
FIG. 5 is a graph showing results of calculation in Example 2.

Results of the calculation in Example 2 are shown in FIG. 5. It is understandable that the polar angle dependence of the transmissivity can successfully be calculated using the Jones matrix obtained by employing the method of the present invention. Also a good agreement with the results of the actually measured transmissivity for comparison was shown, and, therefore, it is understandable that the analytical method of the present invention can help prediction of actually measured transmissivity and so forth, and is useful for designing optical element such as liquid crystal display.

The invention claimed is:

1. A method for analyzing optical characteristics of an optical medium comprising:
    illuminating an optical medium, having an input surface and an output surface of light, with at least three input light beams differed from each other in a polarization state, respectively from a direction inclined by a polar angle θ (0°<θ<90°) with regard to the input surface;
    obtaining polarization states of output light beams coming out from the output surface, corresponded to the input light beams; and
    determining the Jones matrix M which can satisfy the equation (1) below with polarization vectors of the input light beams and polarization vectors of the output light beams:

$$\begin{pmatrix} Es' \\ Ep' \end{pmatrix} = Q' \times M \times Q \times \begin{pmatrix} Es \\ Ep \end{pmatrix} \quad (1)$$

where, Es and Ep are polarization vectors of s-polarization and p-polarization of an input light beam, respectively; Es' and Ep' are polarization vectors of s-polarization and p-polarization of a correspondent output light beam, respectively; Q is a dynamics matrix expressing change in a polarization state of an input light beam going into the optical medium from the air; and Q' is a dynamics matrix expressing change in a polarization state of an output light beam going from the optical medium into the air.

2. The method of claim 1, using matrices expressed by formulas (q1) and (q2) below for Q and Q', respectively, given that the birefringence of the optical medium is approximately 0.1 or smaller:

$$\begin{pmatrix} \dfrac{2n\cos\theta}{n\cos\theta + n_o\cos\theta_o} & 0 \\ 0 & \dfrac{2n\cos\theta}{n\cos\theta_o + n_o\cos\theta} \end{pmatrix} \quad (q1)$$

$$\begin{pmatrix} \dfrac{2n_o\cos\theta_o}{n_o\cos\theta_o + n\cos\theta} & 0 \\ 0 & \dfrac{2n_o\cos\theta_o}{n_o\cos\theta + n\cos\theta_o} \end{pmatrix} \quad (q2)$$

where, n is the refractive index of air, $n_o$ is a mean refractive index of the optical medium to be measured, θ is an incidence angle, and $\theta_0$ is a refraction angle of light in the optical medium.

3. The method of claim 1, further comprising calculating the Stokes parameters as Es, Ep, Es' and Ep' so as to express polarization characteristics of Es, Ep, Es' and Ep'.

4. The method of claim 1 further comprising:
    illuminating the optical medium with at least three input light beams, differed from each other in a polarization state, at least at two azimuthal angles φ (0°<φ<360°), to thereby respectively obtain the Jones matrices which satisfy the equation (1); and
    obtaining an azimuthal angle dependence of at least one parameter which determines the Jones matrices.

5. The method of claim 1 further comprising:
    illuminating the optical medium with at least three light beams differed from each other in a polarization state, from at least two directions differing in polar angle θ (0°<θ<90°), to thereby respectively obtain the Jones matrices which satisfy the equation (1); and
    obtaining a polar angle dependence of at least one parameter which determines the Jones matrices.

6. An apparatus for analyzing an optical medium, comprising:
    a light source;
    an input unit allowing at least three input light beams from the light source, differed from each other in a polarization state, to enter a surface of an optical medium from a direction inclined by a polar angle θ (0°<θ<90°) with regard to the surface;
    a detection unit detecting polarization states of output light beams from the optical medium, corresponded to the input light beams; and a calculation unit determining the Jones matrix M which can satisfy the equation (1) below with polarization vectors of the input light beams and polarization vectors of the correspondent output light beams:

$$\begin{pmatrix} Es' \\ Ep' \end{pmatrix} = Q' \times M \times Q \times \begin{pmatrix} Es \\ Ep \end{pmatrix} \quad (1)$$

where, Es and Ep are polarization vectors of s-polarization and p-polarization of an input light, respectively; Es' and Ep' are polarization vectors of s-polarization and p-polarization of a correspondent output light beam, respectively; Q is a dynamics matrix expressing changes in a polarization state of an input light beam going into an optical medium from the air; and Q' is a dynamics matrix expressing changes in a polarization state of an output light beam going from the optical medium into the air.

7. The apparatus of claim 6, wherein the input unit is capable of allowing at least three input light beams, differed from each other in a polarization state, to enter a surface of an optical medium from at least two directions differing in polar angle θ (0°<θ<90°) and/or azimuthal angle φ (0°<φ<360°).

8. The apparatus of claim 7 further comprising an output unit outputting a graphical expression of at least one parameter of the Jones matrix determined by the calculation unit plotted with respect to polar angle θ and /or azimuthal angle φ.

9. A method for production monitoring of an optical medium comprising:

illuminating an optical medium, having an input surface and an output surface of light, with at least three input light beams differed from each other in a polarization state, respectively from a direction inclined by a polar angle θ (0°<θ<90°) with regard to the input surface; obtaining polarization states of output light beams coming out from the output surface, corresponded to the input light beams;

determining the Jones matrix M which can satisfy the equation (1) below with polarization vectors of the input light beams and polarization vectors of the output light beams, and monitoring a shift from an ideal value of at least one parameter which determines the Jones matrix M:

$$\begin{pmatrix} Es' \\ Ep' \end{pmatrix} = Q' \times M \times Q \times \begin{pmatrix} Es \\ Ep \end{pmatrix} \quad (1)$$

where, Es and Ep are polarization vectors of s-polarization and p-polarization of an input light beam, respectively; Es' and Ep' are polarization vectors of s-polarization and p-polarization of an output light beam, respectively; Q is a dynamics matrix expressing change in a polarization state of an input light beam going into an optical medium from the air; and Q' is a dynamics matrix expressing change in a polarization state of an output light beam going from the optical medium into the air.

\* \* \* \* \*